United States Patent
Koizumi et al.

(10) Patent No.: US 7,820,856 B2
(45) Date of Patent: Oct. 26, 2010

(54) PROCESS FOR PRODUCING α,β-UNSATURATED CARBOXYLIC ACID

(75) Inventors: Atsushi Koizumi, Otake (JP); Kazunori Matake, Otake (JP); Toshihiko Fukuda, Otake (JP); Yuji Fujimori, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 219 days.

(21) Appl. No.: 11/815,907

(22) PCT Filed: Feb. 8, 2006

(86) PCT No.: PCT/JP2006/302117
§ 371 (c)(1), (2), (4) Date: Aug. 9, 2007

(87) PCT Pub. No.: WO2006/085540
PCT Pub. Date: Aug. 17, 2006

(65) Prior Publication Data
US 2009/0182170 A1    Jul. 16, 2009

(30) Foreign Application Priority Data
Feb. 9, 2005 (JP) .............................. 2005-033203

(51) Int. Cl.
*C07C 51/25* (2006.01)
*C07C 51/16* (2006.01)

(52) U.S. Cl. ...................... 562/533; 562/545

(58) Field of Classification Search ........................ None
See application file for complete search history.

(56) References Cited

U.S. PATENT DOCUMENTS 3,876,694 A * 4/1975 Gaenzler et al. ............. 562/522
4,857,239 A * 8/1989 Hurtel et al. ................. 562/896
2006/0014980 A1    1/2006 Kawato et al.

FOREIGN PATENT DOCUMENTS

| JP | 63 198648 | 8/1988 |
| JP | 1 93559 | 4/1989 |
| JP | 2003 192632 | 7/2003 |
| JP | 2004 141828 | 5/2004 |
| WO | 02 083299 | 10/2002 |
| WO | WO 2004/037411 | 5/2004 |

OTHER PUBLICATIONS

U.S. Appl. No. 11/917,422, filed Dec. 13, 2007, Fukuda, et al.
U.S. Appl. No. 12/388,917, filed Feb. 19, 2009, Fujimori, et al.

* cited by examiner

*Primary Examiner*—Paul A Zucker
(74) *Attorney, Agent, or Firm*—Oblon, Spivak, McClelland, Maier & Neustadt, L.L.P.

(57) ABSTRACT

Disclosed is a method for enhancing a yield of an α,β-unsaturated carboxylic acid obtained by liquid-phase oxidation reaction of an olefin or an α,β-unsaturated aldehyde. In particular, there is provided a method for producing an α,β-unsaturated carboxylic acid, wherein the method includes the step of carrying out oxidation reaction of an olefin or an α,β-unsaturated aldehyde in a liquid phase to obtain a reaction mixture containing an α,β-unsaturated carboxylic acid and an α,β-unsaturated carboxylic acid anhydride and the step of bringing the α,β-unsaturated carboxylic acid anhydride into contact with an alcohol or water to obtain an α,β-unsaturated carboxylic acid resulting from decomposition of the α,β-unsaturated carboxylic acid anhydride.

20 Claims, 1 Drawing Sheet

PROCESS FOR PRODUCING α,β-UNSATURATED CARBOXYLIC ACID

TECHNICAL FIELD

The present invention relates to a method for producing an α,β-unsaturated carboxylic acid. In particular, the present invention relates to a method for producing an α,β-unsaturated carboxylic acid by carrying out oxidation of an olefin or an α,β-unsaturated aldehyde in a liquid phase.

BACKGROUND ART

In Patent Document 1 and Patent Document 2, catalysts for producing an α,β-unsaturated carboxylic acid by carrying out oxidation of an olefin or an α,β-unsaturated aldehyde with molecular oxygen in a liquid phase (expressed as "liquid-phase oxidation") and methods for producing the same are disclosed.

Patent Document 1: Japanese Patent Application Laid-Open No. 2004-141,828

Patent Document 2: International Publication No. WO 02/083,299

DISCLOSURE OF INVENTION

Problem to be Solved by the Invention

However, for example, when (meth)acrylic acid is produced by carrying out liquid-phase oxidation of propylene or isobutylene with molecular oxygen, it has been found through the investigation of the present inventors that (meth)acrylic anhydride is simultaneously formed. The oxidation reaction of propylene or isobutylene is a successive reaction, in which an olefin is oxidized to form (meth)acrolein in the first-stage reaction and (meth)acrolein thus formed is oxidized to form (meth)acrylic acid in the second-stage reaction. It is not concluded through what route in the reaction process (meth)acrylic anhydride is synthesized, however, it is presumed that (meth)acrylic anhydride be formed through a reaction of (meth)acrolein, (meth)acrylic acid, and oxygen because the existence of (meth)acrylic anhydride is confirmed only after oxidation of an olefin has proceeded to some extent and concentrations of (meth)acrolein and (meth)acrylic acid have become high.

In Patent Document 1, there is a description on a polymer and oligomer as by-products, however, existence of (meth)acrylic anhydride is not confirmed. Further, in Patent Document 2, there is a description on a formation of methyl formate from an analysis of a reaction liquid, however, there is no description on a formation of (meth)acrylic anhydride. In this manner, when (meth)acrylic acid is produced through liquid-phase oxidation of an olefin or (meth)acrolein, for example, so far no countermeasures have been taken for a formation of (meth)acrylic anhydride which is a by-product, and there still has been considerable room for improvement in a yield of (meth)acrylic acid which is a target material.

It is an object of the present invention to provide a method for enhancing a yield of an α,β-unsaturated carboxylic acid when the α,β-unsaturated carboxylic acid is produced by carrying out oxidation of an olefin or an α,β-unsaturated aldehyde in a liquid phase.

Means for Solving the Problem

The present inventors have diligently researched a method for transforming (meth)acrylic anhydride which is inevitably formed as a by-product in the production of (meth)acrylic acid into a target material in an industrial scale in order to solve the above-mentioned subject. As a result, they have found that (meth)acrylic anhydride can be transformed into a target material by bringing (meth)acrylic anhydride into contact with an alcohol or water, which has become a clue to the present invention. Further, they have found that a yield of (meth)acrylic acid which is a target material can be sharply improved by utilizing the method of bringing (meth)acrylic anhydride, which is formed as a by-product in the case of liquid-phase oxidation of an olefin or (meth)acrolein, into contact with an alcohol or water, and have generalized these information and thus have completed the present invention.

Namely, the present invention relates to a method for producing an α,β-unsaturated carboxylic acid, comprising the steps of:

(a) carrying out oxidation of an olefin or an α,β-unsaturated aldehyde in a liquid phase to obtain a reaction mixture containing an α,β-unsaturated carboxylic acid and an α,β-unsaturated carboxylic acid anhydride; and (b) bringing the α,β-unsaturated carboxylic acid anhydride into contact with an alcohol or water to obtain an α,β-unsaturated carboxylic acid resulting from decomposition of the α,β-unsaturated carboxylic acid anhydride.

EFFECT OF THE INVENTION

According to the method of the present invention, a yield of an α,β-unsaturated carboxylic acid which is a target material can be enhanced.

EXPLANATION OF NUMERALS

Figure 1:
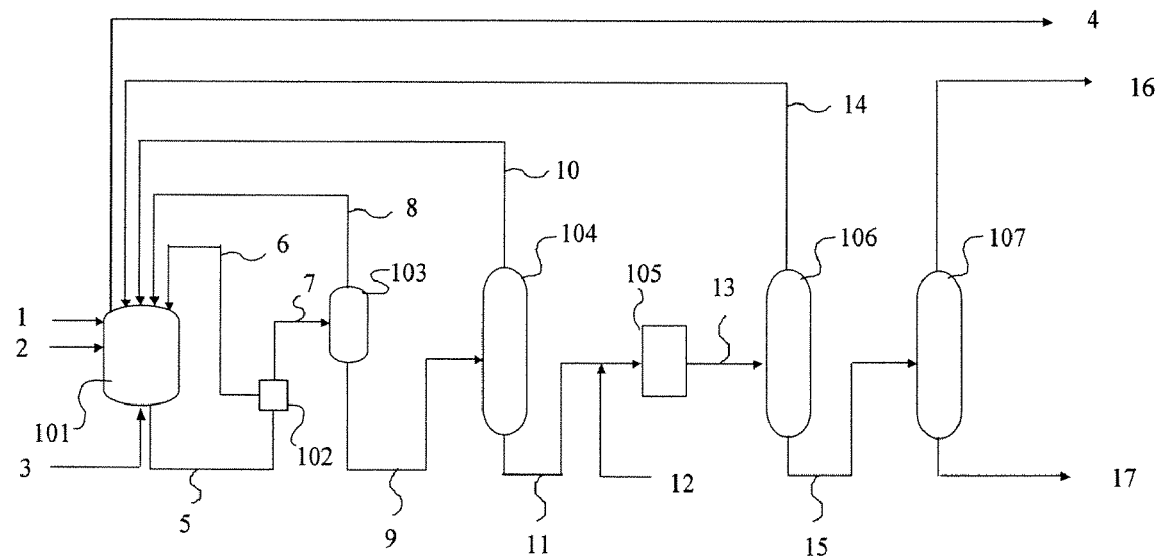
FIG. 1 is a schematic flow diagram showing a constitution of equipment for the production of an α,β-unsaturated carboxylic acid from an olefin as a raw material, which is able to carry out an embodiment of the present invention.

101: Reactor for liquid-phase oxidation
102: Solid-liquid separator
103: Flash tower
104; 106; 107: Multistage distillation column
105: Reactor for esterification/hydrolysis
108: Thin-film evaporator
1 to 19: Pipeline
1: Raw material, solvent-introducing pipeline
2: Inert gas-introducing pipeline
3: Molecular oxygen supply pipeline
4: Off-gas pipeline
5: Reaction liquid-drawing pipeline
6: Catalyst circulating pipeline
7: Reaction liquid after catalyst removal pipeline
8: Olefin circulating pipeline
9: Reaction liquid after olefin removal pipeline
10: Aldehyde circulating pipeline
11: Reaction liquid after aldehyde removal pipeline
12: Alcohol/water supply pipeline
13: After acid anhydride decomposition pipeline
14: Solvent circulating pipeline
15: Reaction liquid after solvent removal pipeline
16: Carboxylic acid-drawing pipeline 17: High-boiling component pipeline
18: High-boiling component including acid anhydride pipeline
19: Acid anhydride pipeline

BEST MODE FOR CARRYING OUT THE INVENTION

The present invention relates to a method which is able to produce an α,β-unsaturated carboxylic acid in a high yield by carrying out oxidation of an olefin or an α,β-unsaturated aldehyde in a liquid phase. Concretely, the α,β-unsaturated carboxylic acid is obtained through liquid-phase oxidation reaction, and besides, an α,β-unsaturated carboxylic acid anhydride formed in the liquid-phase oxidation as a by-product is decomposed by bringing the α,β-unsaturated carboxylic acid anhydride into contact with an alcohol or water to obtain the α,β-unsaturated carboxylic acid.

At first, in the present invention, a step (a) is carried out, in which an olefin or an α,β-unsaturated aldehyde is oxidized in a liquid phase to obtain a reaction mixture containing an α,β-unsaturated carboxylic acid and an α,β-unsaturated carboxylic acid anhydride.

In the present invention, an olefin or an α,β-unsaturated aldehyde can be used as a raw material for the liquid-phase oxidation. As the olefin to be used as the raw material, for example, propylene, isobutylene, or 2-butene can be listed. As the α,β-unsaturated aldehyde to be used as the raw material, for example, acrolein, methacrolein, crotonaldehyde (β-methyl acrolein), or cinnamaldehyde (β-phenyl acrolein) can be listed. Among the olefins, propylene or isobutylene, and among the α,β-unsaturated aldehydes, acrolein or methacrolein are preferable to be used as the raw materials for the liquid-phase oxidation. A small amount of a saturated hydrocarbon and/or a saturated lower aldehyde may be included, as an impurity, in the olefin or the α,β-unsaturated aldehyde to be used as the raw material.

The α,β-unsaturated carboxylic acid to be produced is the one having the same carbon skeleton as the original olefin has in the case that the raw material is the olefin, and the one in which the aldehyde group of the original α,β-unsaturated aldehyde has changed into the carboxyl group in the case that the raw material is the α,β-unsaturated aldehyde. Concretely, acrylic acid is obtained when the raw material is propylene or acrolein and methacrylic acid is obtained when the raw material is isobutylene or methacrolein.

The reaction solvents to be used in the liquid-phase oxidation reaction is not particularly limited and water, alcohols, ketones, organic acids, organic acid esters, hydrocarbons and the like can be used. As the alcohols, for example, tertiary butanol and cyclohexanol can be listed. As the ketones, for example, acetone, methyl ethyl ketone, and methyl isobutyl ketone can be listed. As the organic acids, for example, acetic acid, propionic acid, n-butyric acid, iso-butyric acid, n-valeric acid, and iso-valeric acid can be listed. As the organic acid esters, for example, ethyl acetate and methyl propionate can be listed. As the hydrocarbons, for example, hexane, cyclohexane, and toluene can be listed. Among them, organic acids having 2 to 6 carbon atoms, ketones having 3 to 6 carbon atoms, and tertiary butanol are preferable. These solvents can be used alone or as the mixed solvent of two or more kinds. Further, when at least one compound selected from the group consisting of alcohols, ketones, organic acids, and organic acid esters is used as the solvent, it is preferable to mix the compound with water to form a mixed solvent. The amount of water in the mixed solvent is not particularly limited, however, it is preferably 2% by mass or more to the mass of the mixed solvent and more preferably 5% by mass or more, and preferably 70% by mass or less to the mass of the mixed solvent and more preferably 50% by mass or less. It is desirable that the mixed solvent be homogeneous, however, the mixed solvent may be used in a heterogeneous state.

In the present invention, a solvent which does not contain water and alcohols can also be used effectively as the reaction solvent.

In the present invention, the amount of the olefin or the α,β-unsaturated aldehyde in the reaction solvent in which the liquid-phase oxidation reaction is carried out is preferably 0.1% by mass or more to the reaction solvent existing in the reactor and more preferably 0.5% by mass or more, and 50% by mass or less to the reaction solvent existing in the reactor and more preferably 30% by mass or less.

In the present invention, it is suitable to use a noble metal-containing catalyst prepared, for example, in the following method at the time of the liquid-phase oxidation reaction, however, the noble metal-containing catalyst prepared in a different method or the one on sale may also be used.

The noble metal-containing catalyst can be prepared by dissolving a noble metal compound into a solvent and by reducing the resultant liquid using a reducing agent. Through this reduction, the target noble metal-containing catalyst is deposited. The catalyst can be a supported catalyst in which a noble metal is supported on a carrier, however, the catalyst may be a nonsupported one. The reduction can be carried out in a gas phase, however, it is preferable that the reduction be carried out in a liquid phase. Hereinafter, a liquid-phase reduction method in which a noble metal compound is reduced in a liquid phase will be explained.

The noble metal contained in the noble metal-containing catalyst to be used in the present invention indicates palladium, platinum, rhodium, ruthenium, iridium, gold, silver, rhenium, and osmium. Among them, palladium, platinum, rhodium, ruthenium, iridium, and gold are preferable, and palladium is particularly preferable. Noble metal compounds to be used in the preparation of the noble metal-containing catalyst are not particularly limited, however, for example, chlorides, oxides, acetates, nitrates, sulfates, tetraammine complexes, and acetylacetonate complexes of a noble metal are preferable, chlorides, oxides, acetates, nitrates, and sulfates of a noble metal are more preferable, and chlorides, acetates, and nitrates of a noble metal are particularly preferable.

At first, a noble metal compound solution is prepared by dissolving the foregoing noble metal compound in a solvent. As the solvent, one kind or two or more kinds of solvent selected from the group consisting of water, alcohols, ketones, organic acids, and hydrocarbons can be used. The concentration of the noble metal compound in the noble metal compound solution is preferably 0.1% by mass or more, more preferably 0.2% by mass or more, and particularly preferably 0.5% by mass or more, and preferably 20% by mass or less, more preferably 10% by mass or less, and particularly preferably 7% by mass or less.

Next, the noble metal is reduced by adding a reducing agent to the noble metal compound solution. The reducing agent to be used is not particularly limited and, for example, hydrazine, formaldehyde, sodium borohydride, hydrogen, formic acid, a formate, ethylene, propylene, or isobutylene can be listed.

In the case that the reducing agent is a gas, it is preferable to carry out reduction in a pressure device such as autoclave or the like to increase solubility of the gas into a solution. At that time, it is preferable that the inside of the pressure device be pressurized with the reducing agent. The pressure is preferably 0.1 to 1 MPa (gauge pressure; hereinafter, pressure is expressed in gauge pressure unless otherwise stated).

In the case that the reducing agent is a liquid, there is no limitation to a device for reducing the noble metal and reduction can be carried out by adding a reducing agent to the noble metal compound solution. At this time, the amount of the reducing agent to be used is not particularly limited, however, it is preferably about 1 to 100 moles to 1 mole of the noble metal compound.

The temperature of the reducing system at the time of reduction and the reducing time are variable depending on a reducing method, a noble metal compound to be used, a solvent or a reducing agent, and cannot be exactly affirmed, however, the reducing temperature is preferably 0 to 100° C., and the reducing time is preferably 0.5 to 24 hours in the case of liquid-phase reduction method.

The supported catalyst may be prepared in the same manner as in the case of preparing the nonsupported catalyst except that reduction is carried out with a carrier being present in the noble metal compound solution. As the carrier, for example, activated carbon, carbon black, silica, alumina, magnesia, calcia, titania, or zirconia can be listed. Among them, activated carbon, silica, and alumina are preferably used. A loading ratio of the noble metal is preferably 0.1% by mass or more to the mass of the carrier before the noble metal is supported, more preferably 1% by mass or more, furthermore preferably 2% by mass or more, and particularly preferably 4% by mass or more, and preferably 40% by mass or less to the mass of the carrier before the noble metal is supported, more preferably 30% by mass or less, furthermore preferably 20% by mass or less, and particularly preferably 15% by mass or less.

A precipitate deposited by reduction (a noble metal-containing catalyst) can be filtrated by filtration, centrifugation, and the like. The resultant separated noble metal-containing catalyst is properly dried. The drying method is not particularly limited and various methods can be used. The physical properties of the prepared noble metal-containing catalyst can be confirmed with BET surface area measurement, XRD measurement, CO pulse adsorption measurement, TEM measurement, and the like.

The noble metal-containing catalyst is used in a suspended state in the reaction liquid in which the liquid-phase oxidation is carried out, however, it may be used in a fixed bed. The amount of the noble metal-containing catalyst in the reaction liquid is, as a catalyst existing in the reactor, preferably 0.01 part by mass or more to 100 parts by mass of the solution existing in the reactor in which the liquid-phase oxidation is carried out and more preferably 0.2 part by mass or more, and preferably 50 parts by mass or less to the solution existing in the reactor and more preferably 30 parts by mass or less.

Usually, the liquid-phase oxidation reaction is carried out using a gas containing molecular oxygen. As the gas containing molecular oxygen, air is preferable in view of oxygen concentration and an economic feasibility, however, in the case that the liquid-phase oxidation reaction is carried out at a high-concentration oxygen, pure oxygen or a mixed gas of pure oxygen and air, nitrogen, carbon dioxide or water vapor can be used, if necessary. The amount of molecular oxygen is preferably 0.1 mole or more to 1 mole of the olefin or the α,β-unsaturated aldehyde, more preferably 0.3 mole or more, and furthermore preferably 0.5 mole or more, and preferably 30 moles or less to 1 mole of the olefin or the α,β-unsaturated aldehyde, more preferably 25 moles or less, and furthermore preferably 20 moles or less.

The gas containing molecular oxygen is preferably supplied to the liquid phase in a minute bubble state using a gas distributor. As the gas distributor, for example, a perforated plate, a nozzle, or a porous plate can be listed. A superficial velocity of the gas containing molecular oxygen is preferably 0.2 cm/s or more and more preferably 0.5 cm/s or more, and preferably 30 cm/s or less and more preferably 25 cm/s or less.

The reaction temperature and the reaction pressure at which the liquid-phase oxidation reaction is carried out are properly selected depending on the reaction solvent and the raw materials to be used. The reaction temperature is preferably 60° C. or above and more preferably 70° C. or above, and preferably 200° C. or below and more preferably 150° C. or below. The reaction pressure is preferably not less than the one at which the reaction liquid is liquefied at the reaction temperature, and concretely, it is preferably 0.05 MPa or more and more preferably 0.1 MPa or more. It is desirable to set the reaction pressure at a high value because the oxidation reaction proceeds quicker as the reaction pressure becomes higher, however, it is preferably 10 MPa or less and more preferably 8 MPa or less from the economical point of view.

It is preferable to use polymerization inhibitors in order to prevent polymerization of raw materials or products at a high temperature at the time of the liquid-phase oxidation reaction. As the polymerization inhibitors which can be used on this occasion, for example, phenolic compounds such as hydroquinone and p-methoxy phenol, amine compounds such as N,N'-diisopropyl-p-phenylenediamine, N,N'-di-2-naphtyl-p-phenylenediamine, and N-phenyl-N'-(1,3-dimethylbutyl)-p-phenylenediamine, and N-oxyl compounds such as 4-hydroxy-2,2,6,6-tetramethylpiperidine-N-oxyl or 4-(H—(OCH$_2$CH$_2$)$_n$—O)-2,2,6,6-tetramethylpiperidine-N-oxyl (n being 1 to 18) can be listed. The amount of the polymerization inhibitors to be used is the amount which is necessary to prevent polymerization of the raw materials and the products in the liquid-phase oxidation reaction.

The liquid-phase oxidation reaction can be carried out by either of a batch type operation or a continuous type operation, however, a continuous type operation is industrially preferable. In the case of the continuous type operation, there is no restriction as long as gas-liquid-solid chemical reaction can be carried out. However, for example, a packed-column reactor, a bubble-column reactor, a stirred-tank reactor, a spray-tower reactor and a tray-tower reactor can be used. Among them, a bubble-column reactor and a stirred-tank reactor are preferably used when a liquid-phase oxidation reaction is carried out with a noble metal-containing catalyst being suspended in a reaction liquid. It is possible to carry out a liquid-phase oxidation reaction using, when necessary, an inline multistage-tank reactor in which two or more stages of tanks are arranged in series and a reaction liquid is caused to pass through each tank in order. A retention time of a reaction liquid in a reactor can be properly selected depending on an amount of a noble metal-containing catalyst, a reaction temperature, a reaction pressure, and the like, however, it is preferably 0.1 hour or more and more preferably 0.2 hour or more, and preferably 10 hours or less and more preferably 8 hours or less.

It is apprehended that, in the liquid-phase oxidation reaction, a gas containing molecular oxygen which has passed through a liquid-phase part of the reactor (hereinafter, expressed as "unreacted oxygen gas") forms a detonating gas in a gas-phase part, and hence it is preferable to supply an inert gas such as nitrogen, carbon dioxide, or water vapor to the gas-phase part, or to the liquid-phase part under certain circumstances, to prevent the formation of the detonating gas. The unreacted oxygen gas or a gas in which the unreacted oxygen gas is diluted with the foregoing inert gas contains raw materials and reaction solvents in a low concentration and hence, after the raw materials and the reaction solvents are usually recovered from either of the aforementioned gases, the resultant gas is treated with incinerator and the like from the viewpoint of air pollution control or cost. After that, the treated gas is discharged into the atmosphere. As a method of this recovery, an absorption method, an adsorption method, or the like can be listed.

Although an α,β-unsaturated carboxylic acid can be obtained through the liquid-phase oxidation reaction mentioned above, it has become clear, through the investigation of the inventors, that an α,β-unsaturated carboxylic acid anhydride is formed as a by-product in this liquid-phase oxidation reaction. The acid anhydride formed as the by-product is a compound in which one water molecule is detached from two carboxyl groups of the α,β-unsaturated carboxylic acid which is a target product. Concretely, acrylic anhydride is formed as the by-product in the case that propylene or acrolein is a raw material, and methacrylic anhydride is formed as the by-product in the case that isobutylene or methacrolein is a raw material. Namely, through the liquid-phase oxidation reaction mentioned above, a reaction mixture containing the α,β-unsaturated carboxylic acid and the α,β-unsaturated carboxylic acid anhydride can be obtained.

Therefore, in the present invention, the step (b) of bringing the α,β-unsaturated carboxylic acid anhydride into contact with an alcohol or water to obtain an α,β-unsaturated carboxylic acid resulting from decomposition of the α,β-unsaturated carboxylic acid anhydride is carried out as the next step. By carrying out such a step (b), the α,β-unsaturated carboxylic acid anhydride which is the by-product can be transformed to the α,β-unsaturated carboxylic acid and a yield of the α,β-unsaturated carboxylic acid is improved as a whole. More specifically, by bringing the α,β-unsaturated carboxylic acid anhydride into contact with an alcohol, an α,β-unsaturated carboxylic acid ester and the α,β-unsaturated carboxylic acid resulting from decomposition of the α,β-unsaturated carboxylic acid anhydride can be obtained, and by bringing the α,β-unsaturated carboxylic acid anhydride into contact with water, the α,β-unsaturated carboxylic acid resulting from decomposition of the α,β-unsaturated carboxylic acid anhydride can be obtained.

The α,β-unsaturated carboxylic acid ester obtained by bringing the α,β-unsaturated carboxylic acid anhydride into contact with an alcohol is a useful compound in itself and can be used in an ester form as it is. In this case, the present invention can be regarded as a method for simultaneous production of an α,β-unsaturated carboxylic acid and an α,β-unsaturated carboxylic acid ester. Further, when a yield of the α,β-unsaturated carboxylic acid itself which is an original target product needs to be improved, the α,β-unsaturated carboxylic acid ester can be hydrolyzed into the α,β-unsaturated carboxylic acid. In this case, hydrolysis can be easily carried out by various methods which are conventionally known.

The alcohol to be used in the step (b) is preferably the one having 4 or less carbon atoms, and among them, it is more preferably a primary or a secondary alcohol. Concretely, methanol, ethanol, n-propyl alcohol, isopropyl alcohol, n-butanol, and iso-butanol are preferably used, and among them, in particular, methanol is preferably used. Water to be used in the step (b) is not particularly limited, and for example, distilled water, deionized water, and drinking water can be used.

An alcohol or water to be used in the step (b) can be separately added to a reaction liquid containing an α,β-unsaturated carboxylic acid anhydride. Further, in the case that an alcohol or water is contained in the solvent used in the liquid-phase oxidation reaction, the alcohol or water may not be further added because the alcohol or water which has already been present in the solvent can be used, however, the alcohol or water can also be further added.

The amount of the alcohol or water to be used is preferably 0.8 mole or more to 1 mole of the α,β-unsaturated carboxylic acid anhydride, more preferably 0.9 mole or more, and furthermore preferably 1.05 moles or more, and preferably 20 moles or less to 1 mole of the α,β-unsaturated carboxylic acid anhydride, more preferably 15 moles or less, and furthermore preferably 8 moles or less. In the case that the solvent in which the alcohol or water is contained is used in the liquid-phase oxidation reaction, the amount of the alcohol or water to be used is not particularly limited and the reaction mixture containing the solvent and the α,β-unsaturated carboxylic acid anhydride can be directly used in the step (b). Further, the amount of alcohol or water within the above-mentioned range can also be added to the reaction mixture.

When the α,β-unsaturated carboxylic acid anhydride is brought into contact with an alcohol or water, it is preferable to cause an acid catalyst to coexist in order to increase a reaction rate of the α,β-unsaturated carboxylic acid anhydride. As the acid catalysts, for example, cation exchange resins; organic acids such as benzene sulfonic acid, p-toluenesulfonic acid, methanesulfonic acid, ethanesulfonic acid, and trifluoro acetic acid; mineral acids such as hydrochloric acid, nitric acid, sulfuric acid, and phosphoric acid; and heteropoly acids such as a heteropoly acid and a heteropoly acid salt are preferable. As the cation exchange resins, strongly acidic cation exchange resins such as polystyrolsulfonic acid resin in which a sulfonic group is introduced in a mother nucleus composed of a copolymer of styrene and divinylbenzene, phenolsulfonic acid resin in which a sulfonic group is introduced in a condensate of phenol and formaldehyde, and perfluorosulfonic acid resin in which a sulfonic group is introduced in a copolymer of fluorovinyl ether and fluorocarbon are more preferable. The cation exchange resins are classified, based on geometrical structure, into a gel type and a porous type which has physical micropores, and a porous type cation exchange resin is more preferable in view of improving reaction rate. As such cation exchange resins, for example, Lewatit (trade name) manufactured by Bayer AG and Amberlyst (trade name) manufactured by Rohm and Haas Company can be listed. As the organic acids, p-toluenesulfonic acid is more preferable. As the mineral acids, sulfuric acid is more preferable. As a hetero atom in the heteropoly acid, for example, phosphorous, silicon, boron, aluminum, germanium, titanium, zirconium, cerium, cobalt, chrome, or sulfur can be listed. Further, as a poly atom, for example, at least one atom selected from molybdenum, tungsten, vanadium, niobium, and tantalum can be listed. Concretely, phosphotungstic acid, tungstosilicic acid, tungstoboric acid, phosphomolybdic acid, molybdosilicic acid, molybdoboric acid, phosphomolybdotungstic acid, molybdotungstosilicic acid, molybdotungstoboric acid, phosphovanadomolybdic acid, vanadotungstosilicic acid, and the like can be listed. Further, as the heteropoly acid salt, an acidic metal salt of a heteropoly acid, in which part of hydrogen atoms of the heteropoly acid are substituted, or an acidic onium salt of the heteropoly acid can be listed. As the metal which substitutes part of hydrogen atoms of the heteropoly acid, an alkaline metal such as sodium, potassium, rubidium, or cesium; an alkaline earth metal such as beryllium, magnesium, calcium, strontium, or barium; a transition metal such as copper, silver, zinc, or mercury; and further a typical element such as aluminum, thallium, tin, lead; or the like can be listed. As the acidic onium salt of the heteropoly acid, an ammonium salt which is a salt of the heteropoly acid with ammonia or an amine, a phosphonium salt of the heteropoly acid, or the like can be listed.

In the case that an acid catalyst other than a cation exchange resin, the amount of the acid catalyst to be used is preferably 0.005 mole or more to 1 mole of the α,β-unsaturated carboxylic acid anhydride and more preferably 0.01 mole or more, and preferably 5 moles or less to 1 mole of the α,β-unsaturated carboxylic acid anhydride and more preferably 2 moles or less. In the case that a cation exchange resin is used as an acid catalyst, the amount of the cation exchange resin to be used is preferably 0.005 equivalent mass or more in terms of a cation exchange capacity to 1 mole of the α,β-unsaturated carboxylic acid anhydride and more preferably 0.01 equivalent mass or more, and preferably 5 equivalent mass or less to 1 mole of the α,β-unsaturated carboxylic acid anhydride and more preferably 2 equivalent mass or less.

Further, it is possible to cause a base to coexist instead of the foregoing acid catalyst. As the base, for example, an inorganic base such as a carbonate or a hydroxide of an alkaline metal or an alkaline earth metal, an organic base such as an aliphatic base or an aromatic base, and an aliphatic acid salt of an alkaline earth metal can be used. As a concrete example thereof, sodium carbonate, potassium carbonate, magnesium carbonate, calcium carbonate, sodium bicarbonate, potassium bicarbonate, sodium hydroxide, potassium hydroxide, magnesium hydroxide, calcium hydroxide, trimethylamine, triethylamine, tripropylamine, pyridine, aniline, sodium acetate, sodium oxalate, or the like can be listed.

The amount of the base to be used is preferably 0.005 mole or more to 1 mole of the α,β-unsaturated carboxylic acid anhydride and more preferably 0.01 mole or more, and preferably 5 moles or less to 1 mole of the α,β-unsaturated carboxylic acid anhydride and more preferably 2 moles or less.

As a method for bringing an acid anhydride into contact with an alcohol or water, any one of a batch method, a semi-batch method, and a continuous method can be adopted. From the viewpoint of productivity, a continuous flow method is preferable, and as a reactor of such a method, for example, a tubular reactor, a stirred-tank reactor, and a packed-column reactor can be listed. When a cation exchange resin is used as an acid catalyst, a continuous flow reactor in which a catalyst is packed in a column is preferably used.

The reaction time or the retention time is preferably 0.1 hour or more and more preferably 0.2 hour or more, and preferably 8 hours or less and more preferably 6 hours or less. The reaction temperature is preferably 10° C. or above and more preferably 20° C. or above, and preferably 120° C. or below, more preferably 90° C. or below and furthermore preferably 60° C. or below. The reaction pressure is preferably 500 mmHg (66.7 kPa; in absolute pressure in both cases) or more and more preferably 650 mmHg (86.6 kPa; in absolute pressure in both cases) or more, and preferably 0.5 MPa or less and more preferably 2 MPa or less, though it is possible to carry out the reaction at any one of a reduced pressure, an atmospheric pressure, and elevated pressure.

Although a method for producing an α,β-unsaturated carboxylic acid of the present invention enables to enhance a yield of the α,β-unsaturated carboxylic acid by comprising the foregoing step (a) and step (b), it is preferable to further carry out the step (c) of separating the α,β-unsaturated carboxylic acid and the α,β-unsaturated carboxylic acid anhydride both of which are contained in the reaction mixture obtained in the liquid-phase oxidation reaction, while carrying out the step (b) after the step (c). Hereinafter, a preferable embodiment of a method for producing an α,β-unsaturated carboxylic acid of the present invention including the step (c) will be explained.

In the method of the present invention, it is preferable that, after the liquid-phase oxidation reaction of the step (a) is finished, the used noble metal-containing catalyst and the obtained reaction mixture be separated and the recovered noble metal-containing catalyst be returned to the reactor and be used again. The noble metal-containing catalyst to be returned to the reactor may contain the reaction mixture liquid.

The separation of the noble metal-containing catalyst and the reaction mixture can be carried out at any one of a reduced pressure, an atmospheric pressure, and an elevated pressure. In the case that an olefin is used as a raw material, it is preferable to carry out the foregoing separation at the elevated pressure because any one of propylene, isobutylene, 2-butene, and the like which are olefins to be particularly preferably used in the present invention has a low boiling point. In the case that an α,β-unsaturated aldehyde is used as a raw material, the foregoing separation can be carried out at the atmospheric pressure, however, it may be carried out at the reduced pressure.

In the case that a particle diameter of the noble metal-containing catalyst is large and a specific gravity of the metal-containing catalyst is large, sedimentation by gravity can be carried out as the foregoing separation, however, in the case that the particle diameter of the noble metal-containing catalyst is small and the specific gravity of the metal-containing catalyst is small, centrifugation which uses centrifugal force instead of gravity or filtration in which a filter cake and a filtrate are separated with a partition called filter medium using gravity, elevated pressure, or reduced pressure is preferably used.

At the time of centrifugation, a centrifugal settler such as a cylindrical centrifugal separator, a solids-ejecting separator, a vertical decanter, a vertical multistage decanter, an automatic batch horizontal decanter, a continuous ejecting horizontal decanter, and Centrifuge; and a centrifugal filter such as a batch centrifugal filter, an automatic batch centrifugal filter, an automatic ejecting centrifugal dehydrator, a screw ejecting centrifugal dehydrator, a vibration ejecting centrifugal dehydrator, an extrusion centrifugal dehydrator, an extrusion multistage centrifugal dehydrator, and a screw ejecting (horizontal) centrifugal dehydrator; and the like can be used.

At the time of filtration, a pressure filter such as a pressure Nutsche, a plate pressure filter, a concave plate pressure filter, an Eimco-Burwell pressure filter, a reversible pressure filter, a Kelly filter, a Sweetland filter, a Vallez filter, a horizontal plate pressure filter, a vertical cylindrical pressure leaf filter, a continuous cloth flow filter, a continuous rotary cylindrical pressure filter, a continuous double cylindrical pressure filter, a continuous drum belt pressure filter, a continuous rotary filter press, and a continuous pressure leaf filter; and a vacuum filter such as a vacuum Nutsche, a vacuum leaf filter, a continuous multi room cylindrical vacuum filter, a continuous single room cylindrical vacuum filter, a continuous vertical circular plate vacuum filter, and a continuous horizontal vacuum filter; and the like are used, and in the case that a catalyst in the form of slurry is continuously separated, the cloth flow filter is preferably used.

When a serial multistage tank reactor is used, it is preferable to provide a catalyst separator at an outlet of each tank reactor to separate the noble metal-containing catalyst and the reaction mixture and to return the noble metal-containing catalyst to the original tank and to transfer the reaction mixture to the next tank.

In the method of the present invention, it is preferable that the reaction mixture after the noble metal-containing catalyst has been separated as mentioned above be separated into a mainly unreacted raw material and a reaction mixture containing mainly an α,β-unsaturated carboxylic acid, an α,β-unsaturated carboxylic acid anhydride, and a solvent.

In the case that the raw material is an olefin, it is preferable to separate an olefin which is the unreacted raw material and an α,β-unsaturated aldehyde which is an intermediate product. The olefin and the α,β-unsaturated aldehyde may be separated simultaneously, if possible, however, it is preferable to carry out separation in the order of the olefin and the α,β-unsaturated aldehyde in view of the relations of their boiling points. The olefin to be preferably used in the present invention has a low boiling point, and hence separation of these compounds is preferably carried out by an equilibrium flash distillation. The equilibrium flash distillation is an operation in which a raw material is (, heated when necessary,) flashed into a separator through a pressure-reducing valve to separate into a gas and a liquid corresponding to a temperature and a pressure of the system. It is preferable to set a temperature of the reaction mixture before it is flashed to a reaction temperature or a temperature within a range of a reaction temperature±15° C., and to set a pressure to a reaction pressure or a pressure within a range of a reaction pressure±a reaction pressure×0.3, however, it is more preferable to flash the reaction mixture at its reaction temperature and pressure directly. It is preferable to set a pressure inside the separator to a pressure within a range of 0 MPa to a reaction pressure×0.95. By carrying out the equilibrium flash distillation, the reaction mixture is separated mainly into a vapor containing an olefin as a main component and a liquid containing components other than the olefin. The vapor usually contains the α,β-unsaturated aldehyde, a solvent component, dissolved gases, and the like because the equilibrium flash distillation is a separating operation using only one separation column. When a higher degree separation is needed, an ordinary distillation column such as a tray tower or a packed column can be used. The vapor is preferably recycled to the reactor and used to the reaction after the olefin gas is liquefied with a compression or cooling operation.

In the case that the raw material is an α,β-unsaturated aldehyde, and in the case that the raw material is an olefin and after the separation of the olefin, a separation of an α,β-unsaturated aldehyde can be carried out. For this separation, a conventional distillation operation, extraction operation, membrane-separation operation, and the like can be used, however, it is preferable to use a continuous multistage distillation column. As the foregoing continuous multistage distillation column, the one having 3 plates or more as a number of plates including a reboiler and a condenser is preferable, the one having 4 plates or more is more preferable, and the one having 5 plates or more is furthermore preferable. As such a distillation column, a commonly used distillation column like, for example, a tray tower such as a bubble cap tray tower, a sieve tray tower, a bubble tray tower, or a jet tray tower which causes vapor and gas to contact in a cross flow; a turbo grid tray tower, a ripple tray tower, a dual flow tray tower, or Kittel tray tower which causes vapor and gas to contact in a countercurrent flow; or a baffle tray tower column or a disc donut tray tower which causes gas and liquid to contact in the other manner; and further, for example, a packed column in which an irregular filler such as Raschig ring, a pall ring, an interlock saddle, Dixon packing, or McMahon packing, or a regular filler represented by Sulzer packing is packed, can be used. The foregoing number of plates indicates a theoretical number of plates in both a tray tower and a packed column. A bottom temperature is preferably 150° C. or below, more preferably 120° C. or below, and furthermore preferably 90° C. or below from the viewpoint of preventing polymerization. An operating pressure can be selected from an atmospheric pressure, an elevated pressure, and a reduced pressure within the preferable temperature range of the bottom. Further, part of a liquid of a column top can be refluxed to a distillation column, when it is needed, and a reflux ratio is preferably 0.05 or more and more preferably 0.1 or more, and preferably 20 or less and more preferably 15 or less. It is preferable to use the foregoing polymerization inhibitors to prevent polymerization in a column. It is possible to use bubbling of molecular oxygen at the same time, when it is needed. An α,β-unsaturated aldehyde obtained from the column top may contain a solvent. It is preferable to recycle the liquid of the column top containing an α,β-unsaturated aldehyde to a reactor and to use it again in a reaction. On this occasion, the liquid of the column top may contain a small amount of an α,β-unsaturated carboxylic acid and an α,β-unsaturated carboxylic acid anhydride.

In the method of the present invention, it is preferable to further carry out separation of a solvent from a reaction mixture from which an α,β-unsaturated aldehyde has already been separated. For this separation, a conventional distillation operation, extraction operation, membrane separation operation, and the like can be carried out similarly as in the case of the foregoing separation of an α,β-unsaturated aldehyde. Illustration of a separation by distillation operation as an example is made. For example, it is preferable to use a separation by a continuous multistage distillation column. As such distillation column and operating conditions, it is preferable to use the foregoing distillation column and operating conditions. It is preferable to recover a solvent separated and use it again in a reaction.

In the method of the present invention, it is preferable to further carry out separation of high-boiling component containing an α,β-unsaturated carboxylic acid and an α,β-unsaturated carboxylic acid anhydride from a reaction mixture from which the solvent has already been separated. For this separation, a conventional distillation operation, extraction operation, membrane separation operation, and the like can be carried out similarly as in the case of the foregoing separation of an α,β-unsaturated aldehyde, however, it is preferable to use a separation by means of distillation operation. Separation by a continuous multistage distillation column is preferable, and as such distillation column and operating conditions, it is preferable to use the foregoing distillation column and operating conditions.

Consequently, a crude α,β-unsaturated carboxylic acid can be obtained from a column top. In the case that an α,β-unsaturated carboxylic acid, which is a target product, is (meth)acrylic acid, a crude (meth)acrylic acid obtained here can be used to produce methyl (meth)acrylate through an esterification reaction with methanol or to produce a high purity (meth)acrylic acid through a purifying operation such as crystallization operation. A high-boiling component containing an α,β-unsaturated carboxylic acid anhydride can be obtained from a bottom. In the bottom liquid, an α,β-unsaturated carboxylic acid may be contained. An α,β-unsaturated carboxylic acid anhydride content is preferably 0.1% by mass or more to the mass of the bottom liquid and more preferably 0.5% by mass or more, and preferably 10% by mass or less to the mass of the bottom liquid and more preferably 5% by mass or less.

In the present invention, it is preferable to separate an α,β-unsaturated carboxylic acid anhydride from a high-boiling component containing the α,β-unsaturated carboxylic acid anhydride obtained from the bottom of the column. This separation can be carried out by the foregoing distillation operation, and it is preferable to carry out distillation operation using a thin-film evaporator which is able to instantly heat and evaporate a sample by forming a thin liquid film because an $\alpha,\beta$-unsaturated carboxylic acid anhydride has usually a high boiling point and easily polymerizable as in the case that, for example, the $\alpha,\beta$-unsaturated carboxylic acid anhydride is methacrylic anhydride which has the boiling point of 87° C./13 mmHg (1.73 kPa; in absolute pressure in both cases) (a reagent catalog of Sigma-Aldrich Corporation). As such a thin-film evaporator, a pot still type molecular distillation still, a thin falling film thickener, Smith thin-film evaporator, Luwa thin-film evaporator, Hickman centrifugal molecular distillation still, Othmer centrifugal molecular distillation still, a rotor tray centrifugal molecular distillation still, or the like is preferable, and among them, Smith thin-film evaporator, Luwa thin-film evaporator, or Hickman centrifugal molecular distillation still is more preferably used.

It is preferable to select operating conditions of the thin-film evaporator in such a way that qualities of a target $\alpha,\beta$-unsaturated carboxylic acid anhydride are not deteriorated. A temperature is preferably 30° C. or above and more preferably 50° C. or above. Further, the temperature is preferably 150° C. or below, more preferably 120° C. or below, and furthermore preferably 90° C. or below from the viewpoint of preventing polymerization. A pressure is preferably 0.01 mmHg (1.3 Pa; in absolute pressure in both cases) or more, more preferably 0.1 mmHg (13.3 Pa; in absolute pressure in both cases) or more, and furthermore preferably 1 mmHg (133 Pa; in absolute pressure in both cases) or more, and preferably 100 mmHg (13.3 kPa; in absolute pressure in both cases) or less, more preferably 50 mmHg (6.7 kPa; in absolute pressure in both cases) or less, and furthermore preferably 20 mmHg (2.7 kPa; in absolute pressure in both cases) or less. For example, when methacrylic acid and methacrylic anhydride are present together in a high-boiling component, methacrylic acid and methacrylic anhydride can be distilled out separately or simultaneously by selecting a proper condition among the foregoing operating conditions. Further, the foregoing polymerization inhibitor can be used with the view of preventing polymerization at high temperature.

Further, the foregoing step (b) is carried out with a liquid containing an $\alpha,\beta$-unsaturated carboxylic acid anhydride at the time of before or after the above-mentioned olefin separation, before or after the above-mentioned $\alpha,\beta$-unsaturated aldehyde separation, before or after the above-mentioned solvent separation, or before or after the above-mentioned $\alpha,\beta$-unsaturated carboxylic acid anhydride separation.

Hereinafter, preferable embodiments of the present invention and the constitution of devices to carry out them will be explained by way of the figures, however, the present invention is not restricted by the following.

FIG. 1 is a schematic flow diagram showing a constitution of equipment to produce an $\alpha,\beta$-unsaturated carboxylic acid from an olefin as a raw material. In FIG. 1, raw material, solvent-introducing pipeline 1, inert gas-introducing pipeline 2, off-gas pipeline 4, catalyst circulating pipeline 6, olefin circulating pipeline 8, aldehyde circulating pipeline 10, and solvent circulating pipeline 14 are connected at an upper part of reactor for liquid-phase oxidation 101, and molecular oxygen supply pipeline 3 and reaction liquid-drawing pipeline 5 are connected at a bottom part of reactor for liquid-phase oxidation 101.

In order to carry out a liquid-phase oxidation reaction using such equipment, a solvent and a noble metal-containing catalyst are charged into the reactor for liquid-phase oxidation 101, at first, and an inert gas is introduced into a gas-phase part of the reactor for liquid-phase oxidation, or when it is needed, into a liquid-phase part of the reactor for liquid-phase oxidation through the pipeline 2 to prevent formation of a detonating gas in the gas-phase part. Next, an olefin which is a raw material and a solvent are introduced into the reactor for liquid-phase oxidation 101 through the pipeline 1, and molecular oxygen is introduced into it through the pipeline 3 to carry out a liquid-phase oxidation by bringing the molecular oxygen into contact with the olefin and the noble metal-containing catalyst in the solvent. Unreacted oxygen gas or a gas in which unreacted oxygen gas is diluted with the inert gas is discharged from the pipeline 4. It is also possible to provide an absorption column (not shown in the figure) in the middle of the pipeline 4.

The reaction liquid thus obtained is drawn out from the pipeline 5 together with the noble metal-containing catalyst and the noble metal-containing catalyst is separated at the solid-liquid separator 102. The noble metal-containing catalyst thus separated is returned to the reactor for liquid-phase oxidation 101 through the pipeline 6, and the reaction liquid in which the noble metal-containing catalyst has been separated is sent to the flash tower 103 through the reaction liquid after catalyst removal pipeline 7. At the flash tower 103, a gas containing mainly the olefin is compressed and liquefied by a compressor (not shown in the figure) and returned to the reactor for liquid-phase oxidation 101 from the top of the flash tower 103 through the pipeline 8. Meanwhile, the reaction liquid in which the olefin has been separated is drawn out from the bottom of the flash tower 103 and sent to the multistage distillation column 104 through the reaction liquid after olefin removal pipeline 9. In the case that an aldehyde is a raw material, the flash tower 103, the pipelines 8 and 9 can be omitted and the pipeline 7 can be directly connected to the multistage distillation column 104.

At the multistage distillation column 104, a fraction containing mainly an $\alpha,\beta$-unsaturated aldehyde is returned to the reactor for liquid-phase oxidation 101 from the top of the multistage distillation column 104 through the pipeline 10. Meanwhile, the reaction liquid in which the $\alpha,\beta$-unsaturated aldehyde has been separated is drawn out from the bottom of the multistage distillation column 104 and introduced into the reactor for esterification/hydrolysis 105 through the reaction liquid after aldehyde removal pipeline 11. To the reactor for esterification/hydrolysis 105, an alcohol and/or water which is to be brought into contact with an $\alpha,\beta$-unsaturated carboxylic acid anhydride is supplied through the alcohol/water supply pipeline 12. When an alcohol is used, a corresponding $\alpha,\beta$-unsaturated carboxylic acid ester and a corresponding $\alpha,\beta$-unsaturated carboxylic acid are produced, and when water is used, a corresponding $\alpha,\beta$-unsaturated carboxylic acid is produced and these products are sent to the multistage distillation column 106 through after acid anhydride decomposition pipeline 13. When an alcohol is used, it is also possible to provide a distillation column (not shown in the figure) in the middle of the pipeline 13 to recover unreacted alcohol. At the multistage distillation column 106, a fraction containing mainly the solvent is returned to the reactor for liquid-phase oxidation 101 from the top of the multistage distillation column 106 through the pipeline 14. Meanwhile, the reaction liquid in which the solvent has been separated is drawn out from the bottom of the multistage distillation column 106 and sent to multistage distillation column 107 through reaction liquid after solvent removal pipeline 15. It is also possible to provide a dehydrating column (not shown in the figure) in the middle of the pipeline 15 to remove water produced in the liquid-phase oxidation reaction. Further, an amount of loss of the solvent is supplemented through the pipeline 1.

At the multistage distillation column 107, in the case that an alcohol is used in the reactor for esterification/hydrolysis 105, a corresponding α,β-unsaturated carboxylic acid ester and a corresponding α,β-unsaturated carboxylic acid are drawn out from the top of the multistage distillation column 107 through the carboxylic acid-drawing pipeline 16. Meanwhile, in the case that water is used in the reactor for esterification/hydrolysis 105, a corresponding α,β-unsaturated carboxylic acid is drawn out through the carboxylic acid-drawing pipeline 16. Further, a residue is drawn out from the bottom of the multistage distillation column 107 through high-boiling component pipeline 17.

Figure 2:
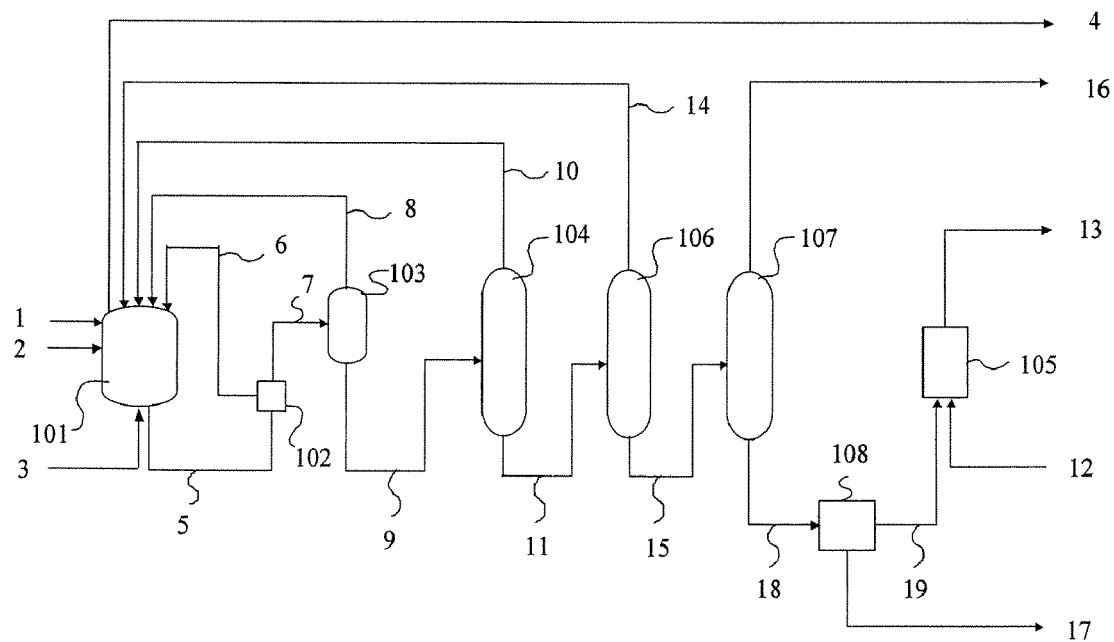
FIG. 2 is another schematic flow diagram showing a constitution of equipment for the production of an α,β-unsaturated carboxylic acid from an olefin as a raw material, which is able to carry out an embodiment of the present invention.

FIG. 2 is another schematic flow diagram showing a constitution of equipment to produce an α,β-unsaturated carboxylic acid from an olefin as a raw material. In FIG. 2, the same procedure as in FIG. 1 is carried out until the multistage distillation column 104 in which an α,β-unsaturated aldehyde is removed. In the next step, the reaction liquid drawn out from the bottom of the multistage distillation column 104, in which the α,β-unsaturated aldehyde has been separated, is introduced into the multistage distillation column 106 through the reaction liquid after aldehyde removal pipeline 11. At the multistage distillation column 106, a fraction containing mainly the solvent is returned to the reactor for liquid-phase oxidation 101 from the top of the multistage distillation column 106 through the pipeline 14. Meanwhile, the reaction liquid in which the solvent has been separated is drawn out from the bottom of the multistage distillation column 106 and sent to the multistage distillation column 107 through the reaction liquid after solvent removal pipeline 15. It is also possible to provide a dehydrating column (not shown in the figure) in the middle of the 15 to remove water produced in the liquid-phase oxidation reaction. Further, an amount of loss of the solvent is supplemented through the pipeline 1.

At the multistage distillation column 107, a fraction containing mainly a target carboxyl acid is drawn out through the carboxylic acid-drawing pipeline 16. Meanwhile, a high-boiling component containing an α,β-unsaturated carboxylic acid anhydride is drawn out from the bottom of the multistage distillation column 107 and sent to thin-film evaporator 108 through high-boiling component including acid anhydride pipeline 18. At the thin-film evaporator 108, a separated fraction containing mainly an α,β-unsaturated carboxylic acid anhydride is sent to the reactor for esterification/hydrolysis 105 through acid anhydride pipeline 19, and a high-boiling component is drawn out as a residue through the high-boiling component pipeline 17. To the reactor for esterification/hydrolysis 105, an alcohol and/or water which is to be brought into contact with an α,β-unsaturated carboxylic acid anhydride is supplied through the alcohol/water supply pipeline 12. When an alcohol is used, a corresponding α,β-unsaturated carboxylic acid ester and a corresponding α,β-unsaturated carboxylic acid are produced, and when water is used, a corresponding α,β-unsaturated carboxylic acid is produced and these products are drawn out through the after acid anhydride decomposition pipeline 13.

EXAMPLES

Hereinafter, the present invention will be explained in more detail by way of the examples.

(Liquid-Phase Oxidation Reaction of Isobutylene)

A stainless steel stirred-tank reactor equipped with a jacket having an inside diameter of 126 mm and a volume of 4 liters was used as a reactor for carrying out a liquid-phase oxidation reaction. The reactor has a structure in which raw materials are supplied from an upper part of the reactor together with a solvent, and a reaction liquid is drawn out from the system while a liquid level of the liquid-phase part of the reaction liquid is kept constant.

To the reactor, 150 g of a palladium metal-containing silica-supported catalyst and 75% by mass tertiary butanol aqueous solution were previously introduced in such a way that a level of the resultant liquid reached a control liquid level. As the palladium metal-containing silica-supported catalyst, the one prepared by dissolving palladium nitrate in water and reducing it with formaldehyde in the presence of a silica carrier to support palladium on the silica carrier was used. The level of the resultant liquid was adjusted in such a way that a volume of the liquid became 3 liters. Nitrogen gas was supplied from an upper part of the reactor and the supply was stopped when a gas-phase part pressure reached 4.8 MPa. A liquid-phase temperature was raised to 90° C. and stabilized at the same temperature for about 10 minutes, and 237 g/hr of liquefied isobutylene and 2,135 g/hr of the solvent were continuously supplied to the reactor. As the solvent, the one prepared by including 200 ppm of p-methoxyphenol as a polymerization inhibitor into 75% by mass tertiary butanol aqueous solution was used. At this time, an average retention time of the resultant liquid phase was 1.0 hour. Subsequently, air was continuously supplied to the liquid-phase part of the reactor at a rate of 800 g/hr from a compressed air bomb through a sparger and the reaction was started while the gas-phase part pressure was maintained. In this state, the reaction was continued for 6 hours, and the obtained reaction mixture was analyzed. As the results, conversion of isobutylene was 46.5%, selectivity to methacrolein was 43.0%, selectivity to methacrylic acid was 23.7%, and selectivity to methacrylic anhydride was 4.9%.

The analysis of the foregoing raw materials and products were carried out using gas chromatography. The conversion of isobutylene, selectivity to methacrolein produced, selectivity to methacrylic acid produced, and selectivity to methacrylic anhydride produced are defined as the following, respectively. As the selectivity to methacrylic anhydride, the following definition based on isobutylene is adopted because methacrylic anhydride is stoichiometrically obtained from two times moles of isobutylene.

Conversion of isobutylene (%)=$(B/A) \times 100$

Selectivity to methacrolein (%)=$(C/B) \times 100$

Selectivity to methacrylic acid (%)=$(D/B) \times 100$

Selectivity to methacrylic anhydride (%)=$(2 \times E/B) \times 100$

In the above formulae, A represents number of moles of isobutylene supplied, B represents number of moles of isobutylene reacted, C represents number of moles of methacrolein produced, D represents number of moles of methacrylic acid produced, and E represents number of moles of methacrylic anhydride produced.

(Separation of Low-Boiling Products and Methacrolein)

The palladium metal-containing silica-supported catalyst was continuously separated by filtration under pressure from the reaction mixture obtained. The filtrate was flashed at a flash tower under atmospheric pressure and unreacted isobutylene was removed. The resultant reaction mixture after isobutylene has been removed was subsequently distilled in batch to separate methacrolein using a glass Oldershaw column having a diameter of 30 and number of plate of 20, under the conditions of the distillation still temperature of about 50° C. and the reflux ratio of 2.0. The composition of the reaction mixture thus obtained was 2.8% by mass of methacrylic anhydride, 30.4% by mass of methacrylic acid, 28.1% by mass of water, and 38.7% by mass of tertiary butanol.

(Esterification/Hydrolysis of Methacrylic Anhydride)

Example 1

A 500 mL four-necked flask equipped with a stirrer, a stirring seal, a thermometer, and a cooling tube was set in a thermostatic oil bath. To the foregoing flask, 300 g of the reaction mixture (containing 28.1% by mass of water) obtained by the foregoing separating operation of low-boiling products and methacrolein and 200 ppm by mass equivalent of p-methoxyphenol as a polymerization inhibitor were measured and introduced. The system was heated to 70° C. while stirred, and 2 mL of a strongly acidic cation exchange resin (IER, manufactured by BayerAG, trade name: Lewatit Catalyst K2621) (dry form; 0.05 equivalent to 1 mole of methacrylic anhydride, ion exchange capacity of 1.3 meq/mL-dry form) was added to the flask as an acid catalyst. After the addition of the acid catalyst, the system was stirred for 2 hours at an inside temperature of 70° C. A small amount of the reaction liquid was sampled and analyzed with HPLC. The analyzing conditions are as follows.

Apparatus: Shimadzu LC-VP series
Column: Synergi4u Fusion-RP 250 mm×4.6 mmID (manufactured by Phenomenox Inc.)
Detecting wave length: 250 nm
Eluant: 2 mM-$KH_2PO_4$ aqueous solution/acetonitrile=70/30
Flow speed: 1.0 ml/min
Oven temperature: 40° C.
Amount of injected sample: 1.0 μL Using these conditions, the results in Table 1 were obtained. The reaction performance was calculated by the following formulae (hereinafter, the same calculation being used in Examples 7 and 8).

Conversion of methacrylic anhydride (ANH) (%)={1−(number of moles of ANH after reaction)/(number of moles of charged ANH)}×100

Selectivity to methacrylic acid (MAA) (%)=(number of moles of produced MAA)/{(number of moles of consumed ANH)×2}×100

Example 2

The same procedure of the reaction was carried out as in Example 1 except that 32 g (1 mole) of methanol (MeOH) was introduced into the flask together with the reaction mixture (containing 28.1% by mass of water) and obtained the results in Table 1. The reaction performance was calculated by the following formulae (hereinafter, the same calculation being used in Examples 3 to 6).

Conversion of methacrylic anhydride (ANH) (%)={1−(number of moles of ANH after reaction)/(number of moles of charged ANH)}×100

Selectivity to methacrylic acid (MAA) (%)=(number of moles of produced MAA)/(number of moles of consumed ANH)×100

Selectivity to methyl methacrylate (MMA) (%)=(number of moles of produced MMA)/(number of moles of consumed ANH)×100

TABLE 1

|  | Added alcohol/water (Added amount) | Acid catalyst (Added amount) | Conversion of ANH (%) | Selectivity to MAA (%) | Selectivity to MMA (%) | Selectivity to (MAA + MMA) (%) |
| --- | --- | --- | --- | --- | --- | --- |
| Example 1 | — | IER (2 ml) | 81.4 | 56.6 | — | — |
| Example 2 | MeOH (1.0 mole) | IER (2 ml) | 95.2 | 40.1 | 133.4 | 173.5 |

Example 3

The solvent is removed by distillation from the reaction mixture obtained by removing low-boiling products and methacrolein, and from the resultant mixed liquid of methacrylic acid and methacrylic anhydride, crude methacrylic acid is separated by vacuum distillation. Subsequently, the resultant separated high-boiling component containing methacrylic anhydride is sent to thin film evaporator to separate into methacrylic anhydride and a residue.

The target material can be obtained by bringing the methacrylic anhydride to be obtained by the foregoing operation into contact with methanol or water. Here, a reagent methacrylic anhydride was used as a model of the methacrylic anhydride to be obtained in such a way mentioned above to carry out esterification/hydrolysis of methacrylic anhydride.

A 100 mL four-necked flask equipped with a stirrer, a stirring seal, a thermometer, and a 50 mL dropping funnel was set in a thermostatic oil bath. To the foregoing flask, 30.8 g of methacrylic anhydride (a reagent manufactured by Aldrich Corporation) and 200 ppm by mass equivalent of p-methoxyphenol as a polymerization inhibitor were measured and introduced. To the flask, 8 mL of the same strongly acidic cation exchange resin as in Example 1 was added as an acid catalyst. Further, 14.4 g (0.45 mole) of reagent methanol was measured into the dropping funnel. Heating of the system was started while the system was stirred. Methanol was dropped little by little into the flask while inside temperature was kept at 50° C., paying attention to heat generation by the reaction. After the dropping of methanol was finished, stirring of the system was continued for 1 hour at 50° C. Consequently, the results in Table 2 were obtained.

Examples 4 to 8

The same procedure was carried out as in Example 3 except that the kind and the amount of addition of alcohol and/or water to be added and the kind and the amount of addition of the acid catalyst to be added were changed as shown in Table 2, the results shown in Table 2 were obtained. As PTS which is an acid catalyst in Table 2, p-toluenesulfonic acid monohydrate (manufactured by Wako Pure Chemical Industries, Ltd.) was used.

TABLE 2

|  | Added alcohol/water (Added amount) | Acid catalyst (Added amount) | Conversion of ANH (%) | Selectivity to MAA (%) | Selectivity to MMA (%) | Selectivity to (MAA + MMA) (%) |
| --- | --- | --- | --- | --- | --- | --- |
| Example 3 | MeOH (0.45 mole) | IER (8 ml) | 97.4 | 86.8 | 99.4 | 186.3 |
| Example 4 | MeOH (0.45 mole) | IER (4 ml) | 73.3 | 82.1 | 117.1 | 199.2 |
| Example 5 | MeOH (0.45 mole) | — | 11.9 | 116.3 | 68.3 | 184.6 |
| Example 6 | MeOH (0.45 mole) | PTS (0.005 mole) | 96.6 | 61.4 | 121.6 | 183.0 |
| Example 7 | $H_2O$ (0.25 mole) | IER (4 ml) | 59.7 | 97.8 | — | — |
| Example 8 | $H_2O$ (0.25 mole) | PTS (0.005 mole) | 55.9 | 93.6 | — | — |

It was recognized that methacrylic anhydride is transformed into a target material (MAA+MMA) by bringing it into contact with methanol or water. The obtained MMA was defined as the target material because it can be transformed into methacrylic acid by hydrolysis treatment which is carried out separately. Consequently, it was recognized that a yield of methacrylic acid can be improved, as a whole, by carrying out the esterification/hydrolysis treatment of methacrylic anhydride subsequent to the foregoing liquid-phase oxidation reaction of isobutylene and the separation of methacrylic anhydride.

What is claimed is:

1. A method for producing acrylic acid, comprising:
   (a) carrying out oxidation of propylene or acrolein in a liquid phase to obtain a reaction mixture comprising acrylic acid and acrylic acid anhydride; and
   (b) bringing the acrylic acid anhydride into contact with an alcohol or water to obtain acrylic acid resulting from decomposition of the acrylic acid anhydride.

2. The method for producing acrylic acid according to claim 1, further comprising:
   (c) separating the acrylic acid and the acrylic acid anhydride from the reaction mixture comprising acrylic acid and acrylic acid anhydride prior to bringing the acrylic acid anhydride into contact with an alcohol or water according to (b).

3. The method for producing acrylic acid according to claim 1, wherein an acid catalyst is present during the carrying out of (b).

4. The method for producing acrylic acid according to claim 3, wherein the acid catalyst is at least one selected from the group consisting of a cation exchange resin, an organic acid, a mineral acid, and a heteropoly acid.

5. The method for producing acrylic acid according to claim 2, wherein an acid catalyst is present during the carrying out of (b).

6. The method for producing acrylic acid according to claim 5, wherein the acid catalyst is at least one selected from the group consisting of a cation exchange resin, an organic acid, a mineral acid, and a heteropoly acid.

7. A method for producing methacrylic acid, comprising:
   (a) carrying out oxidation of isobutylene or methacrolein in a liquid phase to obtain a reaction mixture comprising methacrylic acid and methacrylic acid anhydride; and
   (b) bringing the methacrylic acid anhydride into contact with an alcohol or water to obtain methacrylic acid resulting from decomposition of the methacrylic acid anhydride.

8. The method for producing methacrylic acid according to claim 7, further comprising:
   (c) separating the methacrylic acid and the methacrylic acid anhydride from the reaction mixture comprising methacrylic acid and methacrylic acid anhydride prior to bringing the methacrylic acid anhydride into contact with an alcohol or water according to (b).

9. The method for producing methacrylic acid according to claim 7, wherein an acid catalyst is present during the carrying out of (b).

10. The method for producing methacrylic acid according to claim 9, wherein the acid catalyst is at least one selected from the group consisting of a cation exchange resin, an organic acid, a mineral acid, and a heteropoly acid.

11. The method for producing methacrylic acid according to claim 8, wherein an acid catalyst is present during the carrying out of (b).

12. The method for producing methacrylic acid according to claim 11, wherein the acid catalyst is at least one selected from the group consisting of a cation exchange resin, an organic acid, a mineral acid, and a heteropoly acid.

13. The method for producing acrylic acid according to claim 1, further comprising carrying out the oxidation of propylene or acrolein in the presence of a noble metal-containing catalyst comprising at least one noble metal selected from the group consisting of palladium, platinum, rhodium, ruthenium, iridium, gold, silver, rhenium, and osmium.

14. The method for producing methacrylic acid according to claim 7, further comprising carrying out the oxidation of isobutylene or methacrolein in the presence of a noble metal-containing catalyst comprising at least one noble metal selected from the group consisting of palladium, platinum, rhodium, ruthenium, iridium, gold, silver, rhenium, and osmium.

15. The method for producing acrylic acid according to claim 1, wherein the oxidation of propylene or acrolein in a liquid phase is performed in the presence of a gas comprising molecular oxygen.

16. The method for producing methacrylic acid according to claim 7, wherein the oxidation of isobutylene or methacrolein in a liquid phase is performed in the presence of a gas comprising molecular oxygen.

17. The method for producing acrylic acid according to claim 1, further comprising carrying out the oxidation of propylene or acrolein in the presence of at least one polymerization inhibitor.

18. The method for producing methacrylic acid according to claim 7, further comprising carrying out the oxidation of isobutylene or methacrolein in the presence of at least one polymerization inhibitor.

19. The method for producing acrylic acid according to claim 1, wherein a base is present during the carrying out of (b).

20. The method for producing methacrylic acid according to claim 7, wherein a base is present during the carrying out of(b).

* * * * *